Figure 1:
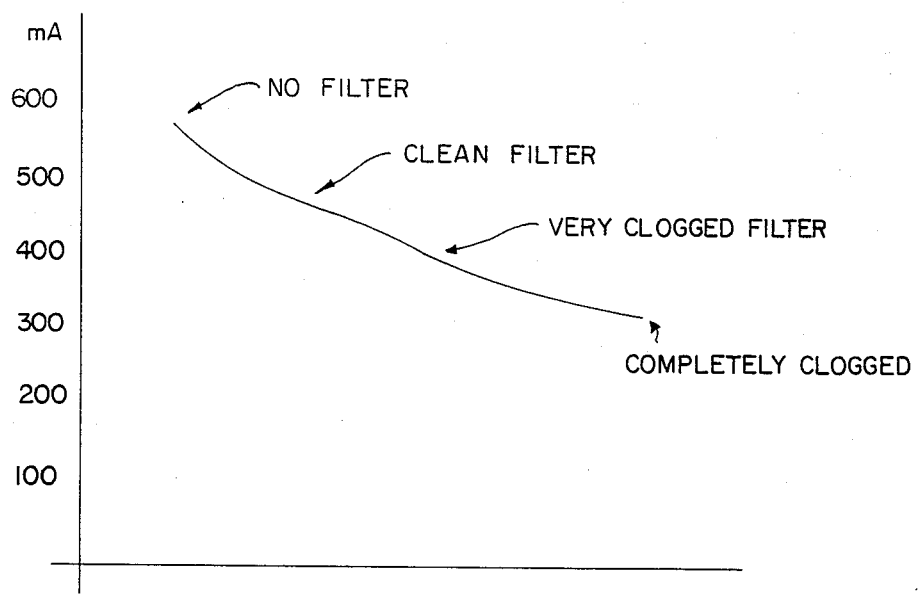

United States Patent [19]

Ponkala

[11] Patent Number: 4,905,687
[45] Date of Patent: Mar. 6, 1990

[54] METHOD AND APPARATUS FOR REGULATING AIR SUPPLIED TO A GAS MASK

[75] Inventor: Jorma Ponkala, Vartsala, Finland
[73] Assignee: Kemira Oy, Espoo, Finland
[21] Appl. No.: 331,500
[22] Filed: Mar. 31, 1989
[51] Int. Cl.$^4$ .............................................. A61M 16/00
[52] U.S. Cl. ............................ 128/204.21; 128/205.12
[58] Field of Search .................... 128/204.21, 204.22, 128/205.12, 206.12, 206.15, 206.17, 204.24, 201.25

[56] References Cited

U.S. PATENT DOCUMENTS

| | | | |
|---|---|---|---|
| 3,414,896 | 12/1968 | Glick et al. | 128/204.21 |
| 4,407,153 | 10/1983 | Furlong et al. | 128/204.24 |
| 4,430,995 | 2/1984 | Hilton | 128/204.21 |
| 4,484,578 | 11/1984 | Durkan | 128/204.24 |
| 4,502,480 | 3/1985 | Yamamoto | 128/201.25 |
| 4,646,732 | 3/1987 | Chien | 128/206.15 |
| 4,676,236 | 6/1987 | Piorkowski et al. | 128/201.25 |

FOREIGN PATENT DOCUMENTS

0094757  11/1983  European Pat. Off. ....... 128/201.25

Primary Examiner—Eugene H. Eickholt
Attorney, Agent, or Firm—Dressler, Goldsmith, Shore, Sutker & Milnamow, Ltd.

[57] ABSTRACT

The invention relates to a method by which the amount of air supplied to a gas mask is kept essentially constant by using the fan motor (1) as a sensor, with the aid of which its power is regulated. The electronic regulation circuit of the invention keeps the air amount constant by regulating the pulse width ratio of the voltage (U1) operating over the motor. The light emitting diode (LED) connected to the control circuit detects when the fan motor is unable to produce the selected amount of air. In order to prevent deep discharge of the battery, the voltage supervising circuit (6) interrupts the current supply to the device when the supplied voltage (SJ) drops below the set limit value.

9 Claims, 3 Drawing Sheets

METHOD AND APPARATUS FOR REGULATING AIR SUPPLIED TO A GAS MASK

The invention relates to a method and a device arrangement for regulating the amount of air supplied to a gas mask, the gas mask comprising a filter, a fan enhancing the air supply passing through it, a motor driving the fan, as well as an electronic circuit including operating switches to guide the operation.

In this connection, the term "gas mask" denotes, besides the gas mask proper, also other breathing coverings and their face parts.

The patent application Nos. EP 0 094 757 and FI 852 272, for instance, disclose gas masks of the type described above. Known gas masks involve the problem of consumption of the accumulators or batteries driving the motor and the risk of deep discharge of the accumulators, which reduces their useful life. Various methods have been proposed to restrict the power consumption (cf. e.g. No. EP-0 094 757).

The GB patent application No. 2 032 284, for instance, discloses controlling of the operating speed of the fan of a mask in terms of the pressure difference detected by a detector. However, such a pressure difference detector is prone to interferences and requires care e.g. when cleaning the mask.

In addition, known devices involve the problem that the air amount supplied to the gas mask varies according to the degree of clogging of the filter. When the filter is new and clean, it lets through more air than what is required by the standards in this case of use. This causes two kinds of problems. On the one hand the accumulators are consumed, and on the other hand, an excessive air flow may make the wearer's head ache and his eyes smart. When the filter is clogged, there is the additional problem of not knowing when the air flow supplied to the gas mask is less than the required amount. On the other hand, an excessive amount of air results in a more rapid clogging of the filter.

As to their construction, present gas masks also have the drawback of the electronics used to control their operation not being sufficiently protected from the damages of the surrounding atmosphere.

The present invention solves the above problems and eliminates the drawbacks of prior known art.

The invention is based on the discovery that the current of the fan motor used e.g. in the gas masks of Kemira decreases gradually as the air flow is obstructed e.g. by the clogging of the filter. This feature of the fan can be used as a kind of sensor, when one wishes to keep the air flow amount constant, although the resistance of the filter or the operating voltage would vary greatly.

In FIG. 1 a typical curve shows how the change of the flow resistance affects the current of the motor.

The curve indicates that the more clogged the filter, the smaller the current consumption. This phenomenon as such stabilizes the air flow, since the ohmic resistance of the coil of the small direct-current motor used in the fan is significant and consequently, the counter-electromotive voltage of the motor and hence also the rotation speed increase as the current decreases.

According to the invention, the air amount supplied to the gas mask is kept essentially constant by regulating the power passing through the fan motor. To achieve this, the gas mask comprises an electronic regulation circuit according to the characterizing part of claim 2.

When the motor itself is used as a sensor, the construction is simplified. The fan and its canals can be washed if needed, since they do not comprise any separate delicate sensors. By means of the regulation circuit, the current supplied to the motor is restricted to a strict minimum, thus increasing its useful life and abating the arising noice. The service life of the filter also increases, since no excessive air is blown through it.

A constant air amount is advantageously provided by controlling the voltage operating over the motor, and the voltage control can also be carried out by pulse-width modulation.

By means of an integration circuit associated with the regulation circuit, the power of the fan motor is adapted steplessly to the wearer's inhalation intensity.

In order to improve the operating characteristics of the gas mask, the control electronics is disposed in a dust- and liquidproof housing, whereby the operating switch of the fan and the selecting switches of the blowing power can be reed relays, which are controlled by means of magnets disposed outside the housing. In this case, no switch inlets, which are difficult to seal, are needed in the housing walls. If needed, the housing may have a gasproof design. Owing to the magnet switches, the electronic circuit is not subject to any mechanical stresses, as it is when mechanical switches are being used.

By means of a detector connected with the control electronic circuit, preferably a light emitting diode, the space is detected, in which the fan motor is unable to produce the selected amount of blown air. Thus an indication which is easily observed by the wearer is obtained, indicating that the accumulator voltage is too low, i.e. the accumulator has been discharged or that the filter is clogged, regardless of the type of filter. This detection may be of vital importance to the wearer.

In order to prevent a deep discharge of the battery that feeds the device, the voltage supervising circuit included in the regulation circuit switches off the current to the motor/device, when the supply voltage drops below a set limit value, thus increasing the useful life of the batteries. Lighter and/or smaller batteries can be used analogously.

As mentioned in the beginning, the concept "gas mask" has a wider signification in this connection. Thus, the present invention is applicable to an integrated gas mask, to a gas mask comprising blowing and/or filter units detached from the face part, and to a breathing covering consisting e.g. of a hood or similar incompletely sealed to the face/head.

Likewise, the present inventive idea, i.e. using a motor as a sensor, is applicable also to other purposes of use, in which a constant flow is to be achieved by a motor.

Figure 2:
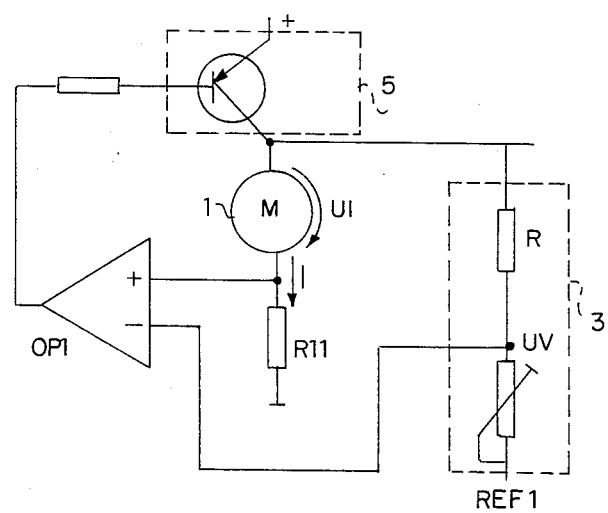
Figure 3:
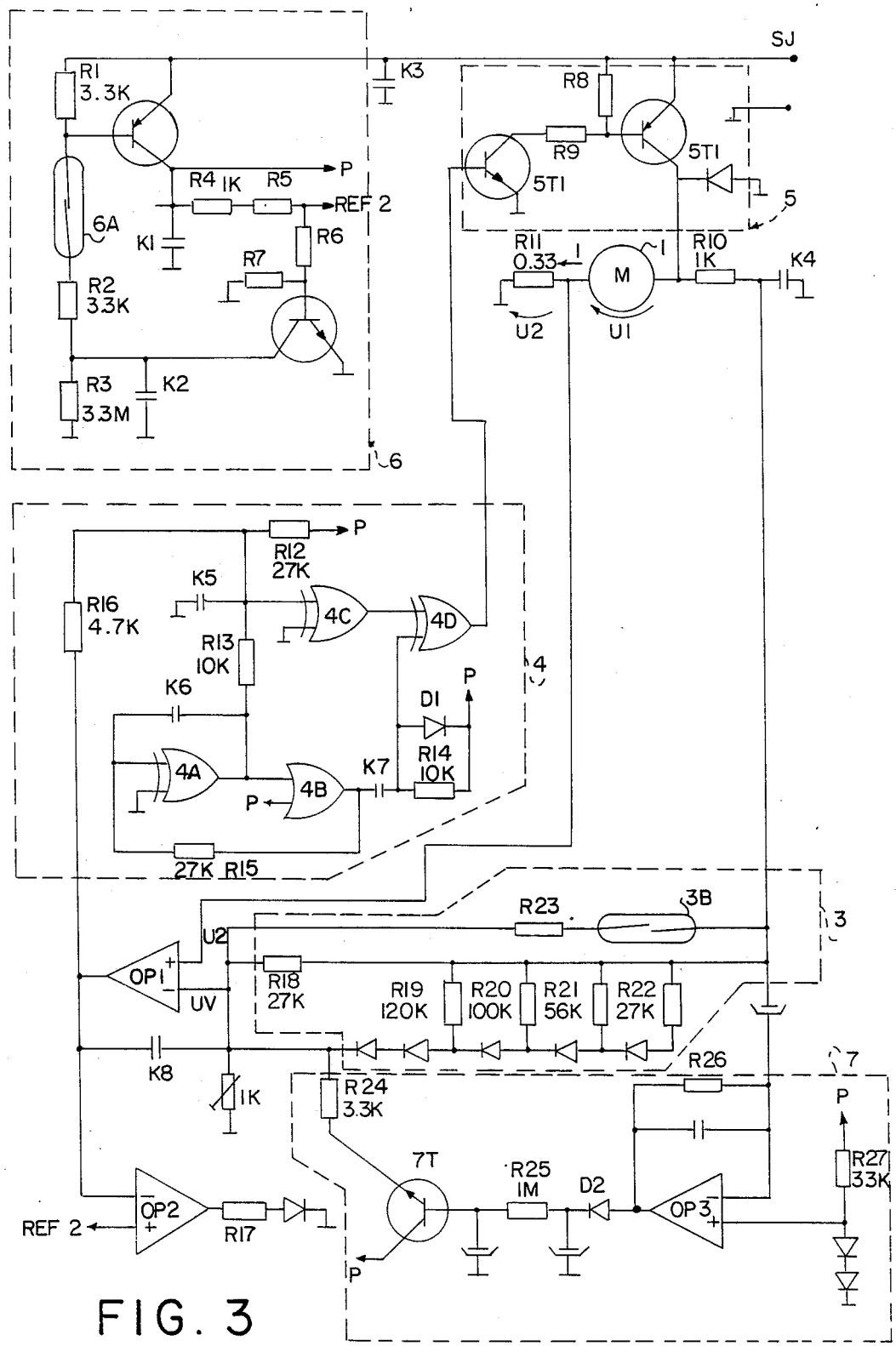

The invention is described in greater detail below by means of an embodiment example and with reference to the drawings, in which FIG. 1 shows the above dependence of the current resistance of a fan motor used in prior known art FIG. 2 shows the principle of the regulation circuit according to the invention and FIG. 3 shows a preferred embodiment of the control electronics of a gas mask.

For the comprehension of the operation, FIGS. 1 and 2 are examined below. It is noted above that the rotation speed of the motor 1 and the voltage U1 operating through it are inverse to the current I.

The stability of the supply air flow of the gas mask can be markedly increased, if a constant current is run through the motor. In this case, the terminal voltage of the motor has to increase as the filter is gradually clogged, since the current is constant.

In principle, the operation amplifier OPI supervises the voltage operating at the poles of the resistor R11, tending to maintain it on the level of a reference voltage UV.

Not even such an arrangement is enough in practice, but the amount of air still decreases as the clogging degree of the filter increases. However, the circuit can be essentially improved, if the reference voltage UV is not fixed, but increases as the voltage in the motor poles increases. By making the resistor R dependent of the voltage, linearization still can be carried out.

FIG. 3 illustrates in greater detail a control electronic circuit in which the principle of the invention is being implemented. The current supply of the circuit derives from an accumulator or a battery (not shown). Although the operation of a circuit switching is understood as such by a person skilled in the art on the basis of the figure, the main points of the operation are described below.

The current switch of the fan motor is accomplished by a reed relay 6A, which is controlled by a magnet (not shown) operating from the outside of the device housing. The partial circuit 6 also comprises voltage supervising components, providing the reference voltage ref2 to the operation amplifier OP2 and the supply voltage P to the gate circuits 4 and the integration circuit 7.

The gate circuit 4 is realized by a microcircuit, the two gates 4A, 4B of which are switched as oscillators. Gate 4C serves as a threshold value detector. Gate 4D including related components (K7, R14 and the diode D1) provides a control to the guide transistor circuit 5, owing to which control the motor, in order to get started, receives a small bottom current having the form of narrow pulses. In this manner, the fan is set into action rapidly enough in spite of the retarding effect of the mass of the fan blades.

Over the guide transistor 5T2 through the motor the pulsed current I is conducted, the value of which is observed by bringing the voltage U2 generated by the current I to the positive inlet (in the figure the pin 5) of the operation amplifier OP1 over the resistor R11.

The said voltage U2 is compared by means of the operation amplifier OP1 to the reference voltage UV brought to its negative inlet (pin 6). The voltage UV is produced from the voltage U1 operating over the motor (more precisely from the sum of voltages U1 and U2, in which the variations of voltage U2 can be left out of account in this connection) by the voltage dividing circuit 3, in which the linearization circuit is carried out by the resistors R18–R22 and the diodes.

By means of the reed relay 3B in the circuit 3 several powers i.e. air flow standard amounts can be selected for the fan motor, by acting on the reference voltage UV. The relay 3B like the switch 6A is guided by magnets disposed outside the housing (not shown). The relay 3B can, of course, be replaced by a potentiometer. In this embodiment example, the reference voltage ref1 is at the earth potential, which is a simple solution. For this reason, the circuit would not bring about the starting of the motor without the above bottom current of the motor provided by the gate 4D.

When an aspiration is generated on the outlet side of the fan, for instance when the device is connected to the mask, the current taken by the fan decreases. If the aspiration is intense enough, the current intake of the motor stops nearly altogether, since the flow amount was already sufficient. When using a mask, such a behaviour is not advisable, and thus there is reason to add the amplifier OP3 to the circuit in the integration circuit 7, which amplifies the slight voltage reduction appearing in the motor poles during the inhalation phase. Subsequent to this amplifier is the top value detector D2. The emitter follower 7T affects over the resistor 24 the reference voltage UV and thus the rotation speed of the motor 1.

In this manner, a circuit that operates nearly ideally is provided, since the device takes account of the inhalation intensity, various filters and their clogging degree, as well as the variations of the battery voltage. By means of the switch 3B a supply air amount of at least 120 l/min can be selected, e.g. for hoods.

The outlet of the operation amplifier OP1 affects the width of the pulses provided by the gate circuit 4 to the guide transistor circuit. Owing to the pulse width modulation, the efficiency coefficient is improved and by modifying the pulse ratio the voltage U1 operating over the motor can be affected.

By controlling the voltage U1, and thus also the rotation speed of the motor, which directly affects the amount of air flowing through, the air amount is kept essentially constant in spite of the variations of the supply voltage and/or the clogging degree of the filter.

The operation amplifier OP2 compares the output level of the operation amplifier OP1 to the reference voltage ref2. When the set level is exceeded, the light emitting diode LED is lighted, the mask wearer receiving thus an indication about the accumulator being run-down and/or the filter clogged. The indication tells that the fan is unable to produce the selected amount of air flow.

In order to prevent that the device be used by mistake with a defective battery, the voltage supervising circuit 6 of the battery prevents the battery from being too much discharged by interrupting the current supply of the device and the motor when the battery voltage drops below the minimum voltage limit (e.g. 4 V).

The regulating method and circuit described above are applicable to various breathing coverings. By means of the fan, an overpressure and the desired air flow are achieved when using a closed mask. When using pen masks and hood models in the breathing coverings, where no pressure differences are generated, the amount of air can however be efficiently controlled.

I claim:

1. A method for regulating the amount of air supplied to the face part of a gas mask or another breathing covering, the gas mask comprising a filter, a fan enhancing the air supply through it, a motor (1) driving the fan, as well as an electronic circuit controlling the operation including operation switches (6A, 3B), characterized in that the fan motor (1) together with the fan blades and the housing surrounding them form a sensor, whereby the current (I) running through the motor (1) and the voltage (U1) operating over the motor detect the variations of the air flow, the power supplied to the fan motor (1) being then regulated on the basis of the said current and voltage.

2. A gas mask or some other face part of a breathing covering, comprising a filter, a fan enhancing the air supply through it, a motor (1) driving the fan, as well as an electronic circuit controlling the operation including operation switches (6A, 3B), characterized in that the electronic regulation circuit (R11, 3, OP1, 4, 5) is set to maintain the air amount supplied to the gas mask essentially constant by regulating the power of the fan motor (1), in that the motor (1) together with the fan blades and the housing surrounding them form a sensor, and in that the power of the motor is regulated on the basis of the current (I) of the motor and the voltage (U1) operating over it.

3. A gas mask according to claim 2, characterized in that the constant air amount is created by controlling the voltage (U1) operating over the motor.

4. A gas mask according to claim 3, characterized in that the voltage control is carried out by pulse width modulation.

5. A gas mask according to claims 2 or 3, characterized in that by means of the regulation circuit connected with the integration circuit (7) the power of the fan motor (1) is steplessly adapted to the wearer's inhalation intensity.

6. A gas mask according to any of claims 2, 3, or 4, characterized in that the control electronics is disposed in a dust- and liquidproof housing.

7. A gas mask according to claim 6, characterized in that the operating switch (6A) of the fan and the switch (3B) selecting the blowing power are carried out by reed relays (6A, 3B) which are guided by magnets disposed outside the housing.

8. A gas mask according to any of claims 2, 3, or 4, characterized in that by means of a detector (LED), preferably a light emitting diode (LED) connected with the control electronic circuit, the space is detected, in which the fan motor is unable to produce the desired selected amount of blown air.

9. A gas mask according to any of claims 2, 3, or 4, characterized in that a voltage supervising circuit (6) interrupts the current supply to the motor (1) when the supplied voltage (SJ) drops below the set limit value.

* * * * *